(12) United States Patent
Giraudet et al.

(10) Patent No.: US 9,389,438 B2
(45) Date of Patent: Jul. 12, 2016

(54) METHOD FOR DETERMINING EYE AND HEAD MOVEMENT OF AN INDIVIDUAL

(71) Applicants: ESSILOR CANADA LTEE, Ville Saint-Laurent (CA); Universite de Montreal, Montreal (CA)

(72) Inventors: Guillaume Giraudet, Montreal (CA); Jocelyn Faubert, Montreal (CA); Rafael Doti, Montreal (CA); Eduardo Lugo, Laval (CA)

(73) Assignees: ESSILOR CANADA LTEE/LTD, St. Laurent (CA); Université de Montréal, Montréxal (CA)

( * ) Notice: Subject to any disclaimer, the term of this patent is extended or adjusted under 35 U.S.C. 154(b) by 0 days.

(21) Appl. No.: 14/420,062

(22) PCT Filed: Jul. 4, 2013

(86) PCT No.: PCT/CA2013/050515
§ 371 (c)(1),
(2) Date: Feb. 6, 2015

(87) PCT Pub. No.: WO2014/022931
PCT Pub. Date: Feb. 13, 2014

(65) Prior Publication Data
US 2015/0212342 A1   Jul. 30, 2015

(30) Foreign Application Priority Data
Aug. 7, 2012   (EP) .................................... 12179531

(51) Int. Cl.
*A61B 3/113*   (2006.01)
*G02C 13/00*   (2006.01)
(Continued)

(52) U.S. Cl.
CPC .............. *G02C 13/005* (2013.01); *A61B 3/113* (2013.01); *A61B 5/1114* (2013.01);
(Continued)

(58) Field of Classification Search
CPC ............ G02C 13/00; G02C 7/06; G02C 7/02; A61B 3/113; A61B 5/11; G06T 7/20
USPC .................................. 351/177, 169, 209, 204
See application file for complete search history.

(56) References Cited

U.S. PATENT DOCUMENTS 6,827,443 B2 *  12/2004  Fisher .................... A61B 3/113
                                                    351/209
8,142,017 B2    3/2012   Drobe et al.
(Continued)

FOREIGN PATENT DOCUMENTS

EP        2221657        8/2010
WO   WO 2008/104695     9/2008
(Continued)

OTHER PUBLICATIONS

International Preliminary Report on Patentability and Written Opinion of the International Searching Authority, issued Feb. 10, 2015 for International Application No. PCT/CA2013/050515 (5 pages).
(Continued)

*Primary Examiner* — Euncha Cherry
(74) *Attorney, Agent, or Firm* — Monique A. Vander Molen; Gardere Wynne Sewell LLP

(57) ABSTRACT

Method for determining the relative amplitude of eye and head movements of an individual, comprising: —a target providing step during which a list of visual targets comprising at least two different visual targets is provided; —a reference positioning step; —a reference target providing step during which a reference target comprising a visual and auditory target is provided; —a reference target gazing step during which the individual gazes at the reference target; —a peripheral target providing step during which a peripheral target comprising a visual and auditory target is provided; —a peripheral target gazing step during which the individual gazes at the peripheral target; and, —a rotation measurement step during which the angle of rotation of the individual's head and the angle or rotation of the individual's eyes are measured.

25 Claims, 3 Drawing Sheets

(51) Int. Cl.
*A61B 5/11* (2006.01)
*G06T 7/20* (2006.01)
*G02C 7/02* (2006.01)

(52) U.S. Cl.
CPC ............... *A61B 5/1121* (2013.01); *G06T 7/20* (2013.01); *G02C 7/027* (2013.01); *G02C 13/003* (2013.01); *G06T 2207/30201* (2013.01)

(56) References Cited

U.S. PATENT DOCUMENTS

2007/0103641 A1 5/2007 Bonnin
2010/0002191 A1 1/2010 Drobe
2012/0002191 A1 1/2012 Van Neste et al.

FOREIGN PATENT DOCUMENTS

WO WO 2009/044080 9/2009
WO WO 2010/015962 2/2010

OTHER PUBLICATIONS

European Search Report and Opinion for EP 12179531.4 dated Jan. 30, 2013 (4 pages).
Jalie, M., Progressive lenses Part 2, The new generation. In: Continuation Education and Training, Module 2, Part 6, Lens Dispensing Today, Jun. 17, 2005, pp. 35-45.

* cited by examiner

METHOD FOR DETERMINING EYE AND HEAD MOVEMENT OF AN INDIVIDUAL

CROSS REFERENCE TO RELATED APPLICATIONS

This application is a U.S. national stage application of International Application No. PCT/CA2013/050515 filed Jul. 4, 2013, which claims the benefit of priority to EP Application No. 12179531.4, filed Aug. 7, 2012; the entirety of each of said applications is incorporated herein by reference, and to the maximum extent allowed.

FIELD OF THE INVENTION

The invention relates to a method for determining relative amplitude of eye and head movements of an individual and a method of determining stability of the eye and head movement strategy of an individual.

BACKGROUND

It is known that individuals have different propensity to move either their eyes or their head when successively looking in different directions.

Such propensity can be of importance when producing ophthalmic lenses.

For example, as disclosed in US Publication No. 2010/0002191, such propensity can be taken into account in order to determine a compromise between the correction of the foveal vision and that of the peripheral vision when producing an ophthalmic lens.

For a wearer who prefers to move his eyes in order to view an off-axis object, the lens manufacturer may provide an ophthalmic lens having a larger zone of the ophthalmic lens that corrects the wearer's foveal vision. Thus, the image of an object viewed by the wearer is correctly formed on the retina, for a greater interval of the angle of rotation of the eyes.

Whereas, for a wearer who prefers to move his head, and thus who usually looks through the ophthalmic lens in a restricted zone located around the centre of the ophthalmic lens, a larger peripheral zone is adapted for the peripheral vision.

International Publication No. WO2009/044080 discloses a method of adapting the addition values of the anterior and posterior faces of a progressive ophthalmic lens not only so as to obtain substantially the addition value of the ophthalmic lens that is prescribed but also to adapt a feature of use of the ophthalmic lens according to the eye and head movements of the wearer.

This adaptation of the feature of use of the progressive ophthalmic lens corresponds to a customization of the progressive ophthalmic lens. It is carried out in order to improve a sensation of the wearer that occurs when he changes his sight direction. In this way, an increased comfort and use of the progressive ophthalmic lens is obtained.

As illustrated with the previous examples, since the propensity to move either the eyes or the head becomes an important parameter when designing a progressive ophthalmic lens, it is important to provide methods for determining the relative amplitude of eye and head movements of an individual that are more and more precise.

The inventors have observed that the known "head/eye" movement coordination tests turn out to present precision defects.

The discussion of the background of the invention herein is included to explain the context of the invention. This is not to be taken as an admission that any of the material referred to was published, known or part of the common general knowledge as at the priority date of any of the claims.

SUMMARY

One object of the invention as described herein is to provide a method for determining the relative amplitude of eye and head movements of an individual that does not present the drawbacks mentioned hereinabove, in particular a more precise method than the prior art methods.

To this end, what is described herein includes a method for determining the relative amplitude of eye and head movements of an individual, the method comprising:
- a target list providing step during which a list of visual targets comprising at least two different visual targets is provided,
- a reference positioning step during which the individual is positioned in a reference position,
- a reference target providing step during which a reference target is provided, the reference target comprising a reference visual target and a reference auditory target being placed substantially at the same position in space, in front of the individual in the reference position, and so that the virtual line between the individual's head in the reference position and the reference target is substantially perpendicular to the vertical plane defined by the individual's shoulders in the reference position,
- a reference target gazing step during which the individual gazes at the reference target,
- a peripheral target providing step during which a peripheral target is provided, the peripheral target comprising a peripheral visual target and a peripheral auditory target being placed substantially at the same offset position with respect to the reference target, the visual target being randomly selected from the list of visual targets,
- a peripheral target gazing step during which the individual gazes at the peripheral target without moving his shoulders, his head and eyes being oriented towards the peripheral target,
- a rotation measurement step during which the angle of rotation of the individual's head and the angle of rotation of the individual's eyes in order to pass from gazing the reference target to gazing the peripheral target are measured, and wherein the reference gazing step, the peripheral target providing step, the peripheral target gazing step and the rotation measurement steps are repeated at least twice by randomly placing the peripheral target at different offset positions.

Advantageously, the method according to the invention provides more precise measurements of the relative amplitude of eye and head movements of an individual.

In particular, the inventors have observed that when measuring the relative amplitude of eye and head movements of an individual, combining auditory and visual targets with the visual target randomly selected in a list of different visual targets significantly increases precision of the measurements.

In the sense of what is described herein, the precision of a method, also called reproducibility or repeatability, is the degree to which repeated measurements under unchanged conditions show the same results.

According to further embodiments which can be considered alone or in combination, are the following:
- the peripheral visual target is horizontally offset with respect to the reference visual target, and/or
- the reference and peripheral visual targets are placed at the individual's eye level, and/or during the peripheral target providing step, the peripheral target is placed so that for the individual, the angle between the peripheral and reference targets is greater than or equal to 20°, and smaller than or equal to 80°, and/or the visual targets of the list of visual targets are distinguishably identifiable by the individual, and/or the visual targets of the list of visual targets are selected among alphanumeric symbols, and/or the auditory targets consist of a white noise signal with a sound pressure level greater than or equal to 30 dB, and smaller than or equal to 100 dB, and/or the white noise is generated by a noise generator used to control the random selection of the visual targets from the list of visual targets, and/or the reference target gazing step and/or the peripheral gazing step have a duration of at least 500 ms, and/or the time between the reference target gazing step and the peripheral target providing step is smaller than or equal to a fifth of the duration of the peripheral gazing step, and/or when repeating the peripheral target providing step, the peripheral target gazing step and the rotation measurement steps, the peripheral target is randomly placed in two offset positions substantially symmetrical relative to the position of the reference target.

According to another aspect, what is described herein relates to a method of determining the stability of the eye and head movement strategy of an individual, wherein the method comprises:

a first measuring stage during which the relative amplitude of eye and head movement of an individual is determined using at least a first method according to the invention, and a further measuring stage, during which the relative amplitude of eye and head movement of the individual is determined using a further method similar to methods described above, wherein the reference and peripheral targets consist of identical visual targets.

According to a further aspect, what is described herein relates to a computer program product comprising one or more stored sequence of instructions accessible to a processor and which, when executed by the processor, cause the processor to carry out at least the reference target providing step, peripheral target providing step, and rotation measurement step, for example, all the steps, of the method described herein.

Furthermore, what is described herein relates to a computer readable medium carrying out one or more sequences of instructions of the computer program product according to the invention.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/ or transform data represented as physical, such as electronic, quantities within the computing system's registers and/or memories into other data similarly represented as physical quantities within the computing system's memories, registers or other such information storage, transmission or display devices.

Embodiments described herein may include apparatuses for performing the operations herein. These apparatuses may be specially constructed for the desired purposes, or may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magneticoptical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, the embodiments described herein are not described with reference to any particular programming language. It will be appreciated that a variety of programming languages may be used to implement the teachings of the inventions as described herein.

BRIEF DESCRIPTION OF THE DRAWINGS

Other features and advantages of the present invention will become apparent from the following description of non-limiting embodiments, with reference to the attached drawings in which.

DESCRIPTION

Figure 1:
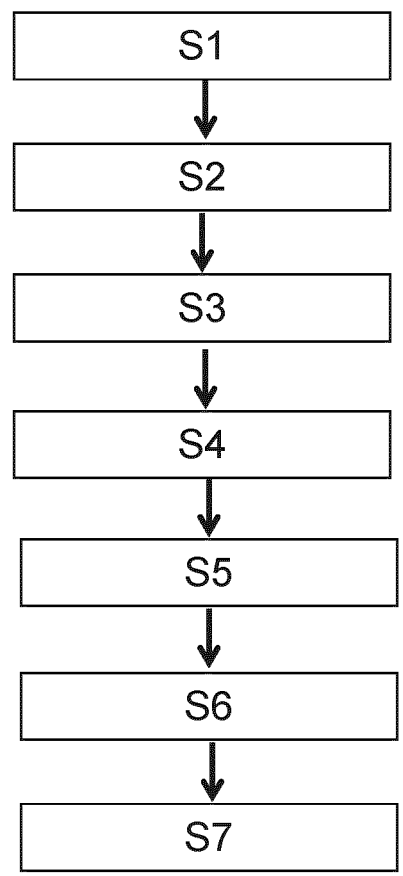
FIG. 1 a representation of the different steps of a method according to at least one embodiment described herein.

According to an embodiment illustrated on FIG. 1, the method for determining the relative amplitude of eye and head movements of an individual comprises:

a target list providing step S1, a reference positioning step S2, a reference target providing step S3, a reference target gazing step S4, a peripheral target providing step S5, a peripheral target gazing step S6, and a rotation measurement step S7.

The reference gazing step S4, the peripheral target providing step S5, the peripheral target gazing step S6, and the rotation measurement steps S7 are repeated at least twice by randomly placing a peripheral target at different offset positions.

During the target list providing step S1, a list of visual targets comprising at least two different visual targets is provided.

In the sense of the invention, two visual targets are considered different when an individual, after having view the first visual target for 500 milliseconds (ms), ms can distinguish the second visual target from the first visual target in less than 500 ms with a resting period of at least 1 second (s) between each moment the individual views the first and second visual targets.

For example, the visual targets of the list of visual targets may be selected among alphanumeric symbols, numbers, letters, symbols, images, geometrical objects, such as n-branches starts etc.

Having different visual targets adds a surprise effect to the method, indeed the individual does not know in advance which visual targets he will be asked to gaze at.

According to an embodiment described herein, the visual targets of the list of visual targets are distinguishably identifiable by the individual.

In the sense of the invention, two visual targets are considered distinguishably identifiable when the two visual targets are different, and the individual can identify each target in less than 500 ms.

For example, the visual targets of the list of visual targets may be selected among Latin alphabet, if the individual is European, and among Chinese characters, if the individual is Chinese.

The inventors have observed that the precision of the method described herein is improved when the visual targets are distinguishably identifiable by the individual even though the individual is not required to identify the visual targets.

The list of visual target may comprise a number of visual targets greater than two. For example the list of visual target may comprise the 26 letters of the Latin alphabet.

Increasing the number of visual targets advantageously provides the possibility of increasing the number of time the reference gazing step S4, the peripheral target providing step S5, the peripheral target gazing step S6, and the rotation measurement steps S7 can be repeated without having the individual anticipate the visual target that may appear. Therefore, the measuring steps can be repeated a number of times while keeping the surprise effect for the individual, thus maintaining a high precision to the measuring method.

During the reference positioning step S2, the individual is positioned in a reference position.

During the reference target providing step S3, a reference target is provided.

The reference target comprises a reference visual target and a reference auditory target.

The reference visual targets is not necessarily selected from the list of visual targets provided during the target list providing step, the reference visual target may be a LED or any other photonic device.

Figure 2:
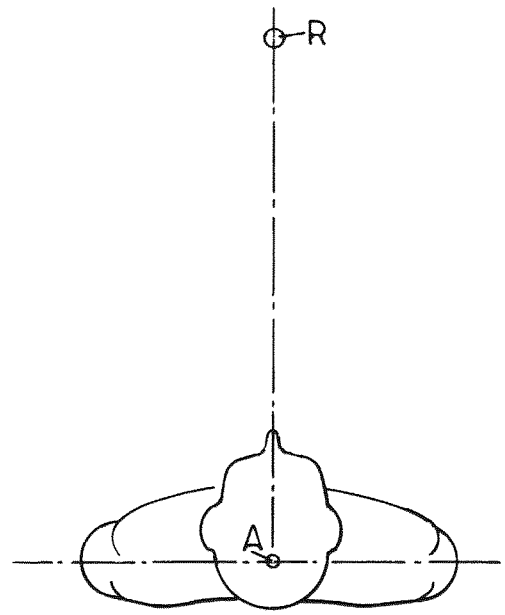
FIGS. 2 and 3 illustrate a principle of measuring eye and head movements for an individual.
Figure 3:
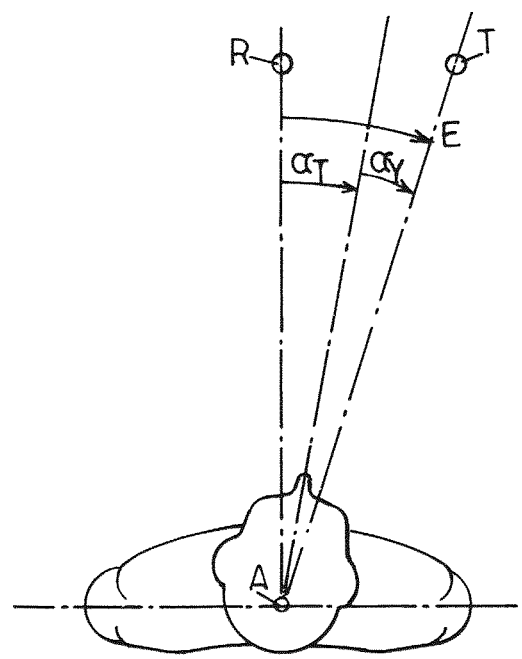

The reference target, denoted R on FIGS. 2 and 3, is placed in front of the individual in the reference position, so that the virtual line between the individual's head in the reference position, and the reference target, is substantially perpendicular to the vertical plane defined by the individual's shoulders in the reference position.

The reference visual and auditory targets are placed substantially at the same position in space.

During the reference gazing target S4, the individual positioned in front of the reference target, in the reference position, gazes at the reference target. The head and eyes of the individual are then oriented towards the reference target.

A peripheral target, denoted T on FIG. 3, is provided during the peripheral target providing step S5.

The peripheral target comprises a peripheral visual target and a peripheral auditory target being placed substantially at the same offset position with respect to the reference target.

The peripheral visual target is randomly selected from the list of visual targets. The selection of the peripheral visual target being random, the individual does not know in advance which visual target he will be gazing at.

The inventors have observed that the use of different visual targets randomly selected in combination with auditory target significantly improves the precision of the measurements.

According to an embodiment described herein, the reference and peripheral auditory targets consist of a white noise signal with a sound pressure level greater than or equal to 30 dB, for example, greater or equal to 50 dB and smaller than or equal to 100 dB, for example, 80 dB.

In the sense of the invention, a white noise is a random signal with a flat power spectral density.

The inventors have observed that the precision of the method is improved when using a white noise as auditory targets.

Preferably, the peripheral target is offset horizontally with respect to the reference target, in order to characterize the horizontal movements of the wearer's head and eyes.

According to an embodiment described herein, the reference and peripheral targets are placed at the individual's eye level so as to simplify the measurements.

The angular displacement of the peripheral target with respect to the reference target is called angular offset and denoted E.

According to an embodiment described herein, the angular offset is greater than or equal to 20°, for example, greater than or equal to 30° and smaller than or equal to 80°, for example, smaller than or equal to 60°, in order to measure significant head and eye movements when having the individual gaze the peripheral target.

During the peripheral target gazing step S6, the individual is asked, starting from the reference position, to gaze at the peripheral target T without moving his shoulders. In order to do this, the individual rotates his head partially and his eyes partially (figure FIG. 3), so that the direction of his gaze passes from the reference target R to the peripheral target T.

In FIG. 3, $\alpha_T$ denotes the angle of rotation of the individual's head, also called angular deviation of the head, in order to pass from the reference position of viewing the reference target to the peripheral position of viewing the test target, and $\alpha_Y$ is the angle of rotation of the eyes performed at the same time by the individual.

The angular offset E is therefore equal to the sum of the two angles $\alpha_T$ and $\alpha_Y$.

During the rotation measurement step S7, the angle of rotation of the individual's head $\alpha_T$ and the angle of rotation of the individual's eyes $\alpha_Y$, in order to pass from gazing the reference target to gazing the peripheral target, are measured.

The center of the head A is taken as a measurement point for the angles in a horizontal plane containing this point and the two targets R and T.

The quotient of the angular deviation of the head $\alpha_T$ by the angular offset E may then be calculated. This quotient is equal to unity for an individual who exclusively turned the head to pass from the reference target to the peripheral target, and zero for an individual who only turned his eyes.

An eye/head movement gain G can be calculated for the individual. The gain G may be defined by a predetermined increasing function of the quotient of the angular deviation of the head $\alpha_T$ by the angular offset E.

For example, the gain G may be directly equal to the quotient of $\alpha_T$ divided by E: $G=\alpha_T/E$. An individual that essentially rotates his eyes to look at the peripheral target thus has a value for gain G close to zero, and an individual that essentially rotates his head to gaze at the same peripheral target has a value for G close to unity.

According to embodiments described herein, the reference gazing step, the peripheral target providing step, the peripheral target gazing step, and the rotation measurement steps, are repeated at least twice, preferably 6 to 30 times, for example, 24 times, by randomly placing the peripheral target at different offset positions so as to provided different measurements of the rotation angles.

According to an embodiment described herein, when repeating the peripheral target providing step, the peripheral target gazing step, and the rotation measurement steps, the peripheral targets are randomly placing in two offset positions substantially symmetrical relative to the position of the reference target, so as to have angular offset E identical in absolute value.

The inventors have observed that the method's method precision is improved when the reference target gazing step and/or the peripheral gazing step have a duration greater than or equal to 500 ms. So as to reduce the time of the method, the reference target gazing step and/or the peripheral gazing step should have a duration smaller than or equal to 5 s, for example, 4 s.

For example, the reference target gazing step has a duration of 2 s, and the peripheral gazing step has a duration of 1 s.

According to an embodiment of the invention, the time between the reference target gazing step and the peripheral target providing step is smaller than or equal to a fifth of the duration of the peripheral gazing step.

Preferably, the time between the reference target gazing step and the peripheral target providing step is as small as possible for example, smaller than or equal to a tenth of the duration of the peripheral gazing step.

According to an embodiment of the invention, the noise generator used to generate the white noise for the auditory targets is used to randomize selection of the visual peripheral targets from the list of visual target, in order to assure a good statistical random selection.

The offset position of the peripheral target may also be randomly selected using the white noise generator in order to provide random sequences in series that are different and not numeric based.

Figure 4:
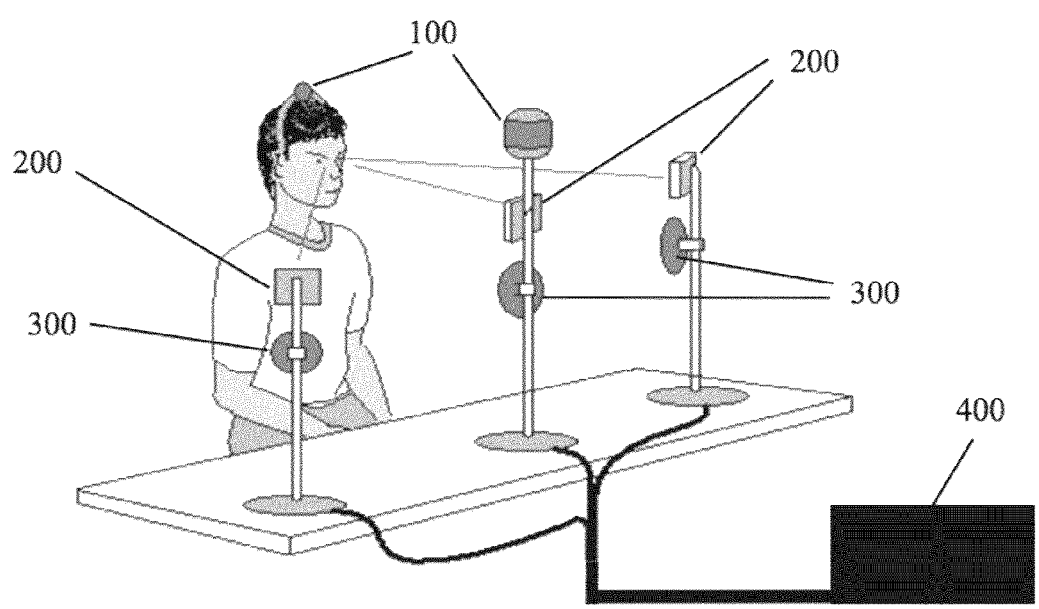
FIG. 4 represents a measuring device that can be used to implement a method according to at least one embodiment described herein.

FIG. 4 illustrates a system that may be used to implement a method according to the invention.

This system comprises movement tracker devices 100, visual stimuli activators 200, acoustic stimuli activators 300 and a control unit 400.

The visual stimuli activators 200 are devices that provide optic stimuli to the individual under test by means of: light generation (any type of lamp, led, active screen, laser beams, etc), or light reflection (passive screen, mirror or scanner, etc) or light refraction (glass, plastic, elastomeric lenses, optic fibers, etc., as static or dynamic optical devices), or light diffraction, light polarization, screens, glass, plastics, or any combination thereof.

The acoustic stimuli 300 are devices that provide auditory stimuli to the individual under test by means of: sound generation (any type of speaker, sound transducer, vibrator, booster, etc.), sound reflection (static or dynamic screens) or sound refraction (static or dynamic sound lenses, or resonators), or sound diffraction, or any combination thereof.

The movement tracker devices 100 follow and register the movements of the individual under test, particularly the eye and head movements during the test. The data collected by these devices is dumped into the control unit 400 for analysis.

The control unit 400 receives all the data gathered by the movement trackers 100, the feedback signals that could be generated, the acoustic and/or visual activators, the internal interfaces (Programmable Logic Controllers and/or amplifiers and/or signal conditioners and/or transducers and/or detectors and/or sound and noise generator, etc.), the external interfaces (man-machine control panel and/or computer with keypad and/or screen and/or pointing devices, etc.).

The control unit 400 also generates the stimuli sequence and trajectory (fixed, random, open loop or adapted), and provides the energy required by the activators in the right way (electric, light, vibration, etc.) to let them achieve the required testing sensory paradigm.

The control unit 400 may also comprise:
a noise generator to generate a white noise,
a random sequence generator that generates random number sequences,
a sequence stimuli paradigm generator that generates a sequence of stimuli paradigm,
a programmable logic controller (PLC) that keeps the program that structures the whole system, and the execution program that is configurable by the operator or experimenter by means of a human-machine interface,
a human-machine interface that is linked to the PLC allowing the dialog between the operator and the system by means of a display and a keypad,
a peripheral interface that physically links the Central Unit to the outputs (amplifiers, activators, alarms, etc.) and the inputs (feed-back signal conditioners, switches, etc.),
a power supply that provides the electric energy required, and the standard protections, and
a computer that receives data, stores data from the movement's trackers, and\or from the PLC, and can performs the data analysis.

According to an embodiment described herein, the noise generator can be used to generate random number sequences so as to randomize visual targets from the visual target and/or the offset position of the peripheral targets.

According to such an embodiment, the noise signal generated by the noise generator is introduced in an analog input for the PLC, and is converted in a binary code capable of recognize 32768 ($2^{15}$) levels between 0 and 10 Volts DC.

Such input may be feed with the noise signal by means of a potentiometer adjusted to give a mean stable reading of 29700 units in the PLC internal register.

The instantaneous values of that register are changed in random way from zero to 29700 units.

The binary value is converted by the PLC in a decimal number that shows big instability.

By a shift operation the second and third numbers (corresponding to the 10th, and 100th multipliers in the decimal code) are separated, providing a two ciphers decimal random code from 00 to 99.

The selection of the peripheral target and/or the offset of the peripheral target are taken in real time at the moment that each movement is triggered. For example, when the register is equal or greater than 50, the peripheral target is offset on the right of the individual, and when the register is equal or lower than 49, the peripheral target is offset on the left of the wearer.

When providing a visual target list comprising 6 different visual targets, a register containing a starting paradigm, for example, 00623541, is created.

8 positions (or ciphers) are used because the PLC register gives a direct high speed conversion for numbers of 8 ciphers. The ciphers are completed by adding two zeroes.

The instantaneous random number is divided (from 0 to 99) in 12 parts.

A ring shift step is assigned according to the 12 parts as follows: 0 to 12, one cipher shifting; 12 to 23: 2 ciphers shift, and so on.

After each shifting operation, the last cipher different from zero is taken out from the register, at each trial.

A zero is added to the register, for example, 00623541, when ring shifted to the right, 2 steps gives: 41006235, the 5 is taken as first paradigm cipher, and the register is completed by adding a zero, so as to have: 41006230 and so on.

After obtaining the first 5 ciphers combination the last one is imposed without any further operation.

For example, to impose the determination of a total of 24 left-right movements, with 12 of them to the right and 12 to the left, the movements that appear are counted to the left and to the right in two independent counters. The first of the counters that reach the number 12 imposes the movement in the direction corresponding to the other counter.

Further described herein is a method for determining the stability of the eye-head movement strategy of an individual.

The inventors have observed that some individual have stable eye-head movement strategy while other have undefined eye-head movement strategy.

The stability of the eye-head movement strategy may be important information when deciding to take into account the eye-head strategy of an individual for designing an ophthalmic lens. Indeed, it may not appear to be as relevant to customize an ophthalmic lens for an individual when such individual has a non-stable eye-head strategy, whereas such customization may be relevant when the individual's eye-head strategy is stable.

The method for determining the eye-head movement strategy stability of an individual described herein may comprise measuring the relative amplitude of eye and head movement of an individual using at least two different measuring methods.

At least one of these methods is a method according to the invention.

The further method may be similar, in which the reference and peripheral targets consist of identical visual targets.

In the sense of the invention, two visual targets are considered identical when an individual, after having view the first visual target for 500 ms, is unable to distinguish the second visual target from the first visual target in less than 500 ms with a resting period of at least 1 s between each moment the individual views the first and second visual targets.

For example, the further method may consist in having LEDs as reference and peripheral targets.

The methods described herein may be carried out by the wearer in the shop at the retail optician where spectacles provided with corrective lenses are ordered.

The invention has been described above with the aid of embodiments without limitation of the general inventive concept as defined in the claims.

The invention claimed is:

1. A method for determining relative amplitude of eye and head movements of an individual, the method comprising:
    selecting at least two visual targets in a target providing step, the two visual targets being different;
    positioning the individual in a reference position in a reference positioning step;
    providing to the individual a reference target in a target providing step, the reference target comprising at least one of a reference visual target and a reference auditory target, such that the reference target is placed substantially at a same position in space, in front of the individual in the reference position, so that a virtual line between the individual's head in the reference position and the reference target is substantially perpendicular to a vertical plane defined by shoulders of the individual when in the reference position;
    tracking a first reference gaze and generating a first reference gaze information in a reference target gazing step, the first reference gaze information generated when the individual gazes at the reference target, such that the head and eyes of the individual are oriented towards the reference target in the first reference gaze;
    providing to the individual a first peripheral target in a peripheral target providing step, the first peripheral target comprising at least one of a peripheral visual target and a peripheral auditory target, such that the first peripheral target is placed substantially at a same first offset position that is offset with respect to the reference target, the first peripheral visual target being selected at random from the list of visual targets and thereby being randomly provided in the peripheral target providing step;
    tracking a first peripheral gaze and generating a first peripheral gaze information in a peripheral target gazing step, the first peripheral gaze information generated when the individual gazes at the peripheral target without moving the shoulders, such that at least one or both of the head and eyes of the individual are oriented towards the peripheral target in the first peripheral gaze;
    calculating first data in a rotation measurement step, the first data including an angle of rotation ($\alpha_r$) of the head and an angle of rotation ($\alpha_y$) of the eyes based on an angle provided by the first reference gaze information and the first peripheral gaze information, and
    in a repeating step, repeating the reference target gazing step, the peripheral target providing step, and the peripheral target gazing step at least twice, thereby tracking a second reference gaze, generating a second reference gaze information, tracking a second peripheral gaze and generating a second peripheral gaze information for calculating a second data in the rotation measurement step, in which a second peripheral target and a second offset position are each selected at random, followed at least by tracking a third reference gaze, generating a third reference gaze information, tracking a third peripheral gaze and generating a third peripheral gaze information for calculating a third data in the rotation measurement step, in which a third peripheral target and a third offset position are each selected at random.

2. The method according to claim 1, wherein the offset position is horizontal in relation to the reference visual target.

3. The method according to claim 1, wherein the reference and peripheral visual targets are provided at eye level of the individual.

4. The method according to claim 1, wherein during the peripheral target providing step, the first peripheral target is at an offset position from the reference target that is greater than or equal to about 20 degrees and smaller than or equal to about 80 degrees.

5. The method according to claim 1, wherein the at least two visual targets are distinguishable and identifiable by the individual.

6. The method according to claim 1, wherein the at least two visual targets are selected among alphanumeric symbols.

7. The method according to claim 1, wherein the auditory target is a white noise signal having a sound pressure level greater than or equal to about 30 dB and smaller than or equal to about 100 dB.

8. The method according to claim 1, wherein the auditory target is a white noise generated by a noise generator used to control random selection of the at least two visual targets.

9. The method according to claim 1, wherein duration of at least one of the reference target gazing step and the peripheral gazing step is at least 500 ms.

10. The method according to claim 1, wherein a resting time between the reference target gazing step and the peripheral target providing step is less than or equal to a fifth of a duration of the peripheral gazing step.

11. The method according to claim 1, wherein in the repeating step, the second peripheral target includes a peripheral visual target and a peripheral auditory target that are placed at random in second offset positions that are symmetric with respect to the position of the reference target.

12. The method according to claim 1, wherein in the method of claim 1 is further repeated and when further repeated the reference and peripheral targets are identical visual targets.

13. The method according to claim 1, wherein positioning the individual in the reference positioning step includes positioning the individual in an upright position.

14. The method according to claim 1, wherein the angle of rotation ($\alpha_r$) and the angle of rotation ($\alpha_\gamma$) are each obtained by measuring in a horizontal plane from a point taken at or about a center of the head.

15. The method according to claim 1, further comprising obtaining a gain of the head by dividing the angle of rotation ($\alpha_r$) by an angular offset E, in which E is a sum of the angle of rotation ($\alpha_r$) and the angle of rotation ($\alpha_\gamma$).

16. The method according to claim 1, further comprising obtaining a gain of the eyes by dividing the angle of rotation ($\alpha_\gamma$) by an angular offset E, in which E is a sum of the angle of rotation ($\alpha_r$) and the angle of rotation ($\alpha_\gamma$).

17. The method according to claim 1, wherein the repeating step is repeated up to about 30 times.

18. The method according to claim 1, wherein the method of claim 1 is further repeated, in which the reference and peripheral targets are identical visual targets, and a second calculating step measures eye and head amplitude based on a difference obtained when the reference and peripheral targets are different as compared with when the reference and peripheral targets are the same.

19. A system for determining eye and head movement of an individual comprising:
 a visual stimuli unit configured to provide a plurality of visual targets including one as a reference target and more than one as peripheral targets for the individual to gaze at in order to generate one reference gaze information and more than one peripheral gaze information, the more than one peripheral targets provided at random by the visual stimuli unit;
 an auditory stimuli unit configured to provide a plurality of auditory targets including one as a reference target and more than one as peripheral auditory targets, the more than one peripheral targets provided at random by the auditory stimuli unit;
 a tracker unit configured to detect and store head and eye movement data and to generate gaze information, the gaze information including a plurality of gaze directions of the individual including gaze directions provided by any one or more of the reference visual target, the reference auditory target, the more than one peripheral visual target provided at random, and the more than one peripheral auditory target provided at random; and
 a control unit configured to receive the eye and head movement data and the gaze information from the tracker unit, to generate and receive data about the visual targets provided by the visual stimuli unit, and to generate and receive data about the auditory stimuli provided by the auditory stimuli unit, the control unit further configured to calculate a change based on the received data.

20. The system of claim 19, wherein the visual stimuli unit includes a plurality of devices, each device spaced apart, in which at least two of the plurality of devices provide visual stimuli simultaneously or in series.

21. The system of claim 19, wherein the auditory stimuli unit includes a plurality of devices, each device spaced apart, in which at least two of the plurality of devices provide auditory stimuli simultaneously or in series.

22. The system of claim 19, wherein the auditory stimuli unit includes a plurality of auditory stimuli units, the visual stimuli unit includes a plurality of visual stimuli units, and the plurality of auditory stimuli units and the plurality of visual stimuli units are co-located.

23. The system of claim 19, wherein the auditory stimuli unit and the visual stimuli units are coordinated to simultaneously provide the reference target and the more than one peripheral targets.

24. A non-transitory computer readable medium storing a program for causing a computer to execute the method according to claim 1.

25. A system for determining eye and head movement of an individual comprising:
 a non-transitory computer-readable medium;
 program instructions stored on the non-transitory computer-readable medium and executable by at least one processor to:
  generate a reference object that includes an auditory signal from an auditory signaling unit and a visual signal from a visual signaling unit;
  receive reference gaze information about the reference object from a tracking unit;
  analyze the reference gaze information to detect reference head and eye position data;
  generate a peripheral object that includes a peripheral auditory signal from the auditory signaling unit and a peripheral visual signal from the visual signaling unit, the peripheral object offset from the reference object;
  receive peripheral gaze information about the peripheral object from the tracking unit;
  analyze the peripheral gaze information to detect peripheral head and eye position data;
  calculate an angle of rotation ($\alpha_r$) of the head from the reference head position data and the peripheral head position data;
  calculate an angle of rotation ($\alpha_\gamma$) of the eyes from the reference eyes position data and the peripheral eyes position data;
  determine a gain of the head by dividing the angle of rotation ($\alpha_r$) by an angular offset E, in which E is a sum of the angle of rotation ($\alpha_r$) and the angle of rotation ($\alpha_\gamma$); and
  determine a gain of the eyes by dividing the angle of rotation ($\alpha_\gamma$) by an angular offset E, in which E is a sum of the angle of rotation ($\alpha_r$) and the angle of rotation ($\alpha_\gamma$).

* * * * *